United States Patent [19]

Black

[11] Patent Number: 5,129,883
[45] Date of Patent: Jul. 14, 1992

[54] CATHETER
[76] Inventor: Michael Black, 22 Gillespie Crescent, Ottawa, Ontario, Canada, K1V 9X8
[21] Appl. No.: 736,373
[22] Filed: Jul. 26, 1991
[30] Foreign Application Priority Data Jul. 26, 1991 [CA] Canada ............................ 2022019

[51] Int. Cl.⁵ ............................................. A61M 29/00
[52] U.S. Cl. ..................................... 604/101; 604/53
[58] Field of Search .............................. 604/96–104, 604/45–49, 52, 53, 280

[56] References Cited

U.S. PATENT DOCUMENTS

| | | |
|---|---|---|
| 3,435,824 | 4/1969 | Gamponia . |
| 3,516,408 | 6/1970 | Montanti . |
| 3,991,767 | 11/1976 | Miller, Jr. et al. . |
| 4,230,119 | 10/1980 | Blum . |
| 4,610,662 | 9/1986 | Weikl et al. . |
| 4,674,506 | 6/1987 | Alcond . |
| 4,676,778 | 6/1987 | Nelson, Jr. . |
| 4,712,551 | 12/1987 | Rayhanabad . |
| 4,731,055 | 3/1988 | Melinyshyn et al. . |
| 4,751,924 | 6/1988 | Hammerschmidt et al. . |
| 4,781,677 | 11/1988 | Wilcox . |
| 4,832,688 | 5/1989 | Sagae et al. . |

FOREIGN PATENT DOCUMENTS

| | | |
|---|---|---|
| 743368 | 9/1966 | Canada . |
| 921221 | 2/1973 | Canada . |
| 1036887 | 8/1978 | Canada . |
| 1049875 | 3/1979 | Canada . |
| 1050377 | 3/1979 | Canada . |
| 1122494 | 4/1982 | Canada . |
| 1132876 | 10/1982 | Canada . |
| 1153265 | 9/1983 | Canada . |
| 1157728 | 11/1983 | Canada . |
| 1157729 | 11/1983 | Canada . |
| 1158505 | 12/1983 | Canada . |
| 1160128 | 1/1984 | Canada . |
| 1162816 | 2/1984 | Canada . |
| 1255989 | 6/1989 | Canada . |

OTHER PUBLICATIONS

Akaba, N. et al "Management of acute aortic dissections with a cylinder-type balloon catheter to close the entry", *Journal of Vascular Surgery* vol. 3, No. 6, Jun. 1986, pp. 890–894.

Ijima, H. et al "A New Blood-flow Maintainable Balloon Catheter for Closure of the Entry of the Dissecting Aneurysm of the Aorta—An Experimental Study", Dept. of Surgery, Inst. of Clinical Medicine, Univ. of Tsukuba.

Trent, M. S. et al., "A balloon-expandable intravascular stent for obliterating experimental aortic dissection", *Journal of Vascular Surgery* 11:707–17 (1990).

Wright, K. C. et al., "Percutaneous Endovascular Stents: An Experimental Evaluation", *Radiology* 156:69–72 (1985).

Dotter, C. T. et al., "Luminal Expandable Nitinol Coil Stent Grafting: Preliminary Report", *Radiology* 147:259–260 (1983).

Cragg, A. et al., "Nonsurgical Placement of Arterial Endoprostheses: A New Technique Using Nitinol Wire", *Radiology* 147:261–263 (2983).

Maass, D. et al., "Radiological Follow-up of Transluminally Inserted Vascular Endoprostheses: An Experimental Study Using Expanding Spirals", *Radiology* 152:659–663 (1984).

Charnsangavej, C. et al., "Endovascular Stent for Use in Aortic Dissection: An in Vitro Experiment", *Radiology* 157:323–324 (1985).

Palmaz, J. C. et al., "Expandable intraluminal vascular graft: A feasibility study", *Surgery* 99(2):199–205 (1986).

Primary Examiner—John D. Yasko
Attorney, Agent, or Firm—Browdy and Neimark

[57] ABSTRACT

A catheter adapted to be inserted into and advanced through a patient's circulatory system or through any other hollow conduit of the body is disclosed. The catheter of the present invention comprises a shunt section incorporating an elongated conduit having an open, distal end and a closure intermediate the open distal end and the outer terminal end of the catheter. A first inflatable cuff is located at the distal end of the tube while a second cuff is located at a predetermined distance from the first cuff, between the distal end and the closure of the shunt section. A pair of radiographic markers assist in the proper positioning of the cuffs. Means are provided to allow the blood to exit the tube near the proximal end thereof. Inflating and deflating means for the cuffs are also provided.

6 Claims, 1 Drawing Sheet

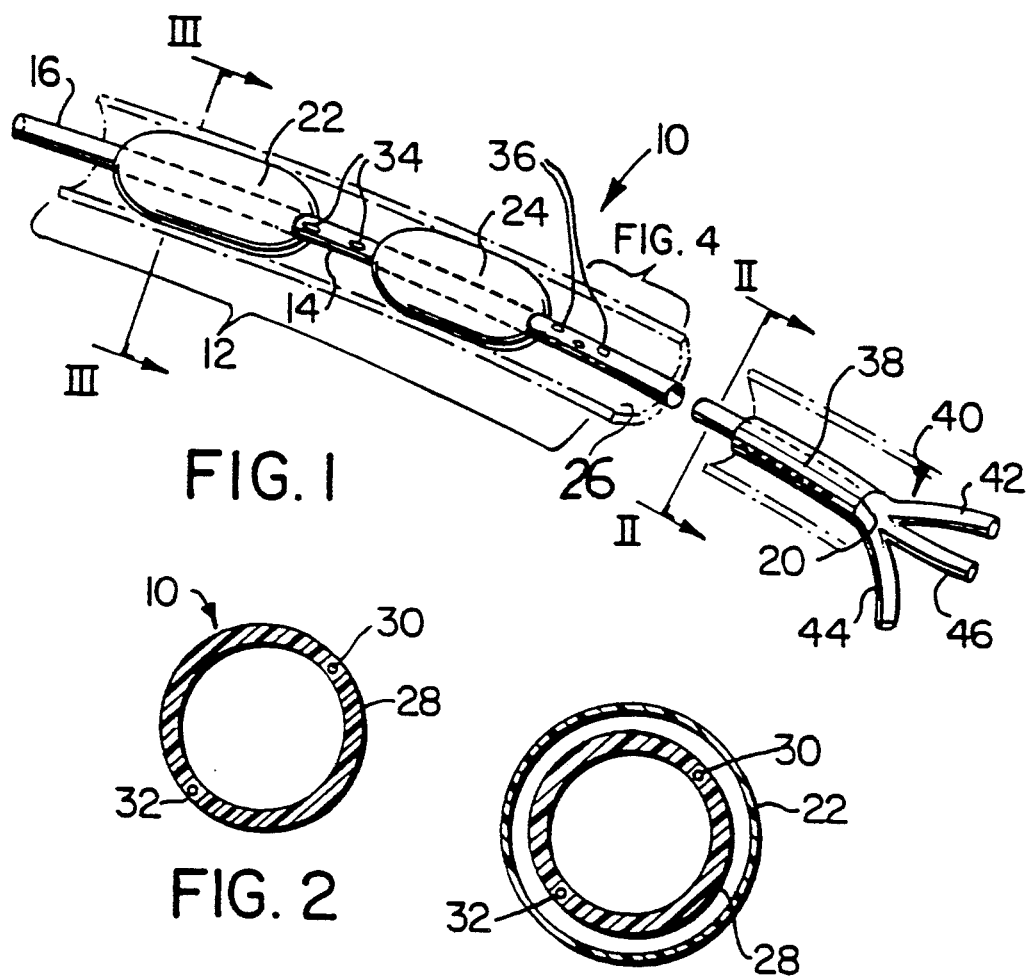
FIG. 1
FIG. 2
FIG. 3
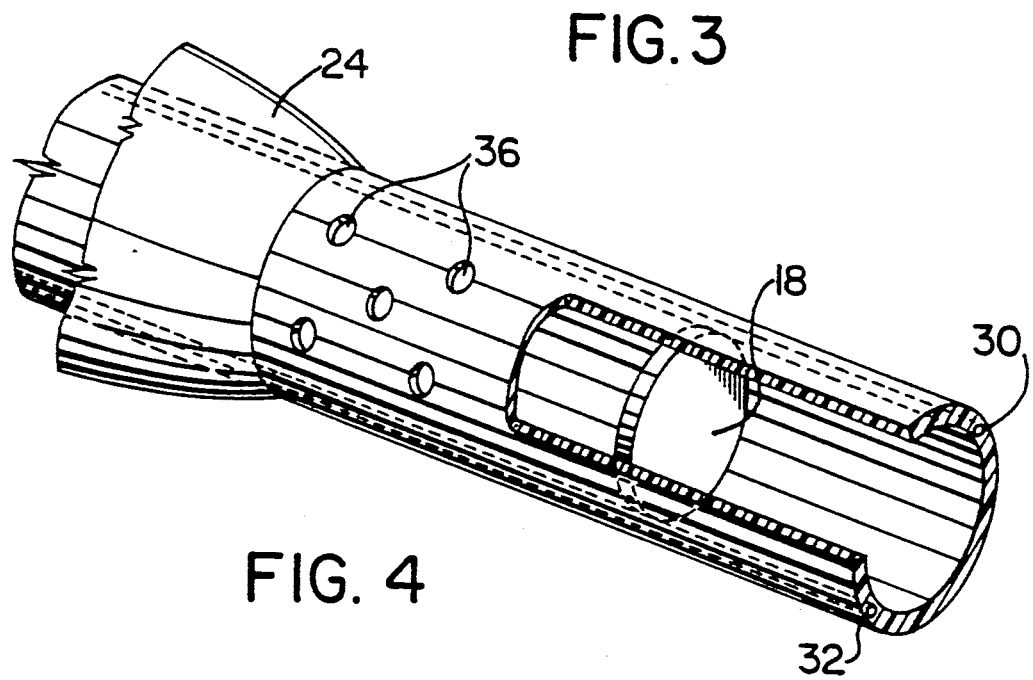
FIG. 4

CATHETER

FIELD OF THE INVENTION

This invention relates to catheters and specifically to a catheter for placement within a mammal which is adapted to interrupt the flow of body fluids through a predetermined area. By way of example, the catheter of the present invention can be used to interrupt and divert blood flow and allow repairs to be effected to a specific vein or artery.

BACKGROUND OF THE INVENTION

The balloon catheter concept is applicable to a wide variety of surgical procedures. The application of the concept has resulted in the construction of balloon-tipped catheters designed specifically for the system in which they are used. Such balloon-tipped catheters include occlusion and arterial embolectomy catheters. Catheters comprising two inflatable balloons are known. For example, U.S. Pat. No. 3,991,767 discloses a tubular unit used in the treatment of an aneurysm. The unit comprises two inflatable cuffs which are adapted to engage the wall of a blood vessel and an open-ended tube that serves to transport the blood. The inflatable cuffs are disposed at either end of the unit and the blood is shunted from one end of the unit to the other. The unit can be introduced into the vessel through an opening made in the vessel for that purpose or can be percutaneously inserted.

In the case of a trauma to a vessel and in order to repair the vessel, it is necessary to have proximal and distal control of the area of the vessel to be operated upon. By way of example, where there is an aortic transection as a result of a blunt trauma, a large mediastinal haematoma obliterates most of the visual landmarks to aid in obtaining vascular control, rendering the placement of vascular clamps a tasks fraught with dangers since further damage may be caused to the underlying neurovascular structures. The catheter of the present invention overcomes the problems inherent with the placement of vascular clamps. Moreover, the use of the catheter of the present invention reduces the anaesthetic time necessary to effect repair of the vessel. In addition, the catheter of the present invention obviates the need for the insertion of an external shunt which would also require manipulation of the vessel. While shunting of blood around the area of vascular occlusion is not always necessary and is often not conducted in order to avoid further manipulation of the injured vessel and concomitant increase in anaesthetic time, shunting may prevent the incidence of post-operative complications.

It is an object of the present invention to provide a catheter which obviates the need for surgical clamps and an external shunt.

SUMMARY OF THE INVENTION

In one broad embodiment, the present invention provides a catheter adapted to be inserted into and advanced through a circulatory system to a desired location in a vessel. The catheter has a shunt section at the distal end thereof. The shunt section incorporates an elongated conduit having an open distal end, a closure intermediate the open distal end and the outer terminal end of the catheter. At least a pair of inflatable cuffs are secured about said conduit at a predetermined distance from each other. The first cuff of said pair is located intermediate the distal end and the second cuff of said pair. The second cuff is located intermediate the first cuff and the closure. A pair of radiographic markers assist in the positioning of the shunt section. The shunt section further comprises means to allow the transport of blood from the shunt section back into the vessel. These means are located intermediate said second cuff and said closure. The catheter further comprises means to inflate and deflate the cuffs.

In another broad embodiment, the invention relates to a catheter adapted for placement within a mammal comprising a shunt section at the distal end thereof adapted to transport body fluids. The shunt section incorporates an elongated conduit having an open distal end, a closure intermediate the open distal end and the outer terminal end of the catheter. The shunt section comprises at least a pair of inflatable cuffs secured about the conduit at a predetermined ,distance from each other. The first cuff of the pair is located intermediate the distal end and the second cuff of the pair. The second cuff is located intermediate the first cuff and the closure. A pair of radiographic markers assist in the proper positioning of the shunt section. The shunt section further comprises means to allow the transport of body fluids out of said shunt section located intermediate said second cuff and said closure as well as means for inflating and deflating the cuffs.

BRIEF DESCRIPTION OF THE DRAWINGS

The invention is illustrated by way of example in the accompanying drawings in which:

FIG. 1 is a perspective view of the catheter in a vessel after inflation of the cuffs;

FIG. 2 is a cross-sectional view of FIG. 1 at II—II;

FIG. 3 is a cross-sectional view of FIG. 1 at III—III; and

FIG. 4 is an enlarged view, partly in cross-section, of the circled area of FIG. 1.

DESCRIPTION OF THE PREFERRED EMBODIMENT

Referring to FIG. 1, the catheter 10 comprises a flexible tube, preferably made of plastic material. The catheter 10 comprises a shunt section 12 which incorporates an elongated conduit 14 having an open distal end 16 and a closure 18, shown in FIG. 4. The closure 18 is located intermediate the open distal end 16 and an outer terminal end 20 of the catheter 10. Secured about the shunt 12 are cuffs 22 and 24 spaced from one another and which are positioned to engage, by way of example as illustrated in FIG. 1, the walls of a blood vessel 26 on either side of the area from which it is desired to divert blood flow or to which it is desired to effect repairs.

The first cuff 22 is located adjacent the distal end 16 of the shunt section 12 while the second cuff 24 is located at a point between the first cuff 22 and the closure 18 of the shunt section 12. As shown in FIG. 3, with respect to cuff 22, each cuff 22 and 24 has an outer gas impermeable layer 28. Fluid such as air is fed into the conduits 30 and 32 which are formed in the wall of the catheter 10, to inflate the cuffs 22 and 24. The conduits 30 and 32 are in communication with the cuffs 22 and 24 by means of apertures through the wall of the catheter 10 which lead into the inside of the cuffs 22 and 24.

A pair of radiographic markers 34 are placed on the shunt section 12 between the two cuffs 22 and 24 to assist in the positioning of the catheter 10 as will be further described below.

The shunt section 12 has a plurality of circumferentially spaced passages 36 located inwardly of and in close proximity to the closure 18 which allow blood which has entered the distal end 16 of the catheter 10 to re-enter the vessel 26 downstream from the cuff 24.

In using the catheter 10 of the present invention, the catheter must first be inserted through the femoral artery in the conventional manner. To do so, the femoral artery is located and punctured. A hollow needle (not shown) is inserted through the aperture made in the femoral artery. A guide wire (not shown) is inserted through the hollow needle into the artery. The hollow needle is removed after insertion of the guide wire. An arterial dilator (not shown) and sheath 38, illustrated in FIG. 1, are then inserted over the guide wire. The dilator is removed. The sheath 38, which is illustrated in FIG. 1, serves to stabilize the catheter in that it holds it in place and prevents blood leakage. The catheter 10 is then lubricated and inserted into the sheath 38 and over the guide wire. The guide wire is then removed. A junction member 40 is then secured to the outer end of the sheath 38 for example by means of a threaded member, not shown. The junction member 40 comprises a distal port 42 and a proximal port 44 which are connected to conduits 30 and 32 respectively. The junction member 40 comprises a third port 46 which, if desired, could be connected to a conduit which would extend through the closure 18 of the shunt section 12 to the terminal end 20 of the catheter and allow the withdrawal of blood and the monitoring of blood pressure.

The catheter 10 is advanced through the artery and placed in proper position through use of the radiographic markers 34. Typically, in the case of a tear in a vessel, such a tear would be first visualized through the introduction of a dye through the femoral artery followed by the introduction and proper positioning of the catheter 10 with the use of the markers 34. The cuffs 22 and 24 are then inflated simultaneously or consecutively through the introduction of fluid, such as air, by means of syringes secured to the distal and proximal ports 42 and 44. Once the cuffs 22 and 24 are inflated, the blood will then be shunted through the damaged region entering the distal end 16 of the shunt 12 and exiting through the apertures 36 adjacent the closure 18 of the shunt 12. Once the damaged vessel has been repaired, the cuffs 22 and 24 are deflated and the catheter 10 and sheath 38 are removed.

Those skilled in the art will appreciate that the described embodiment, while preferred, can be modified to a greater or lesser degree. In particular, while the catheter has been described for use in the circulatory system, it is understood that the catheter of the present invention could also be used in any of the hollow conduits of the body such as the bile ducts, the intestines and the ureter of any mammal. I therefore wish to embody within the scope of the patent which may be granted hereon all such embodiments as reasonably and properly come within the scope of my contribution to the art.

The embodiments of the invention in which an exclusive property or privilege is claimed are defined as follows:

1. A catheter adapted to be inserted into and advanced through a circulatory system to a desired location in a vessel, said catheter having a shunt section at the distal end thereof, said shunt section incorporating an elongated conduit having an open distal end, a closure intermediate the open distal end and the outer terminal end of said catheter, at least a pair of inflatable cuffs secured about said conduit at a predetermined distance from each other, a first cuff of said pair being located intermediate said distal end and the second cuff of said pair; said, second cuff being located intermediate said first cuff and said closure, a pair of radiographic markers to assist in the positioning of said shunt section, means to allow the transport of blood from said shunt section back into the vessel, said means being located intermediate said second cuff and said closure, means for inflating and deflating said cuffs.

2. The catheter of claim 1 wherein each cuff is associated with means for inflating and deflating said cuff.

3. The catheter of claim 2 comprising two cuffs, the first of which is located immediately adjacent the distal end of said tube.

4. The catheter of claim 1 wherein the means to allow the blood to travel back into the vessel comprise a series of circumferentially located apertures in said conduit.

5. A catheter adapted to be inserted into and advanced through a circulatory system to a desired location in a vessel, said catheter having a shunt section at the distal end thereof, said shunt section incorporating an elongated conduit having an open distal end, a closure intermediate the open distal end and the outer terminal end of said catheter, a first and second inflatable cuffs secured about said conduit, the first cuff being located adjacent the distal end of the shunt and the second cuff being located intermediate said first cuff and said closure, a pair of radiographic markers to assist in the positioning of said shunt section, a series of circumferentially located apertures intermediate said second cuff and said closure to allow the blood to travel back into the vessel and a fluid carrying passage associated with each cuff used to inflate and deflate said cuffs.

6. A catheter adapted for placement within a mammal comprising a shunt section at the distal end thereof adapted to transport body fluids, said shunt section incorporating an elongated conduit having an open distal end, a closure intermediate the open distal end and the outer terminal end of said catheter, at least a pair of inflatable cuffs secured about said conduit at a predetermined distance from each other, the first cuff of said pair being located intermediate said distal end and the second cuff of said pair, said second cuff being located intermediate said first cuff and said closure, a pair of radiographic markers to assist in the positioning of said shunt section, means to allow the transport of body fluids out of said shunt section, said means being located intermediate said second cuff and said closure, means for inflating and deflating said cuffs.

* * * * *

UNITED STATES PATENT AND TRADEMARK OFFICE
CERTIFICATE OF CORRECTION

PATENT NO. : 5,129,883
DATED : July 14, 1992
INVENTOR(S) : Michael BLACK It is certified that error appears in the above-identified patent and that said Letters Patent is hereby corrected as shown below:

On the title page: Item

[30] Foreign Application Priority Data

Delete "July 26, 1991", insert therefor -- July 26, 1990 --

Under "OTHER PUBLICATIONS":

second column, line 16      Delete "(2983), insert therefor -- (1983) --

Signed and Sealed this

Fifth Day of October, 1993

*Attest:*

BRUCE LEHMAN

*Attesting Officer*     *Commissioner of Patents and Trademarks*